(12) United States Patent
Huang

(10) Patent No.: US 6,823,740 B1
(45) Date of Patent: Nov. 30, 2004

(54) METHOD OF SELECTING A CRITICAL PLANE FOR MULTI-EVENT FATIGUE LIFE PREDICTION

(75) Inventor: Liping Huang, Canton, MI (US)

(73) Assignee: Ford Motor Company, Dearborn, MI (US)

(*) Notice: Subject to any disclaimer, the term of this patent is extended or adjusted under 35 U.S.C. 154(b) by 0 days.

(21) Appl. No.: 10/604,901

(22) Filed: Aug. 26, 2003

(51) Int. Cl.[7] ............................................. G01D 1/00
(52) U.S. Cl. ........................... 73/787; 73/791; 73/804; 702/180
(58) Field of Search ..................... 73/783, 787, 791, 73/799, 804, 811; 702/42, 180

(56) References Cited

U.S. PATENT DOCUMENTS

| 4,801,421 A | * | 1/1989 | Ackerson et al. ........... 376/249 |
| 5,079,955 A | | 1/1992 | Eberhardt |
| 5,164,669 A | * | 11/1992 | Namkung et al. ........... 324/209 |
| 5,531,123 A | * | 7/1996 | Henkel ........................ 73/795 |
| 5,732,200 A | | 3/1998 | Becker et al. |
| 5,835,758 A | | 11/1998 | Nochur et al. |
| 5,852,793 A | * | 12/1998 | Board et al. ................... 702/56 |
| 6,018,716 A | | 1/2000 | Denardo et al. |
| 2003/0018511 A1 | | 1/2003 | Bicknell et al. |

* cited by examiner

*Primary Examiner*—Max Noori
(74) *Attorney, Agent, or Firm*—David B. Kelley

(57) ABSTRACT

A method and system for selecting a critical plane. The critical plane can then be used to leverage off of uniaxial fatigue theory to predict the fatigue life of an object experiencing multiple stress inducing events. The fatigue life is based on calculating a single critical plane that encompasses all the stress inducing events.

20 Claims, 5 Drawing Sheets

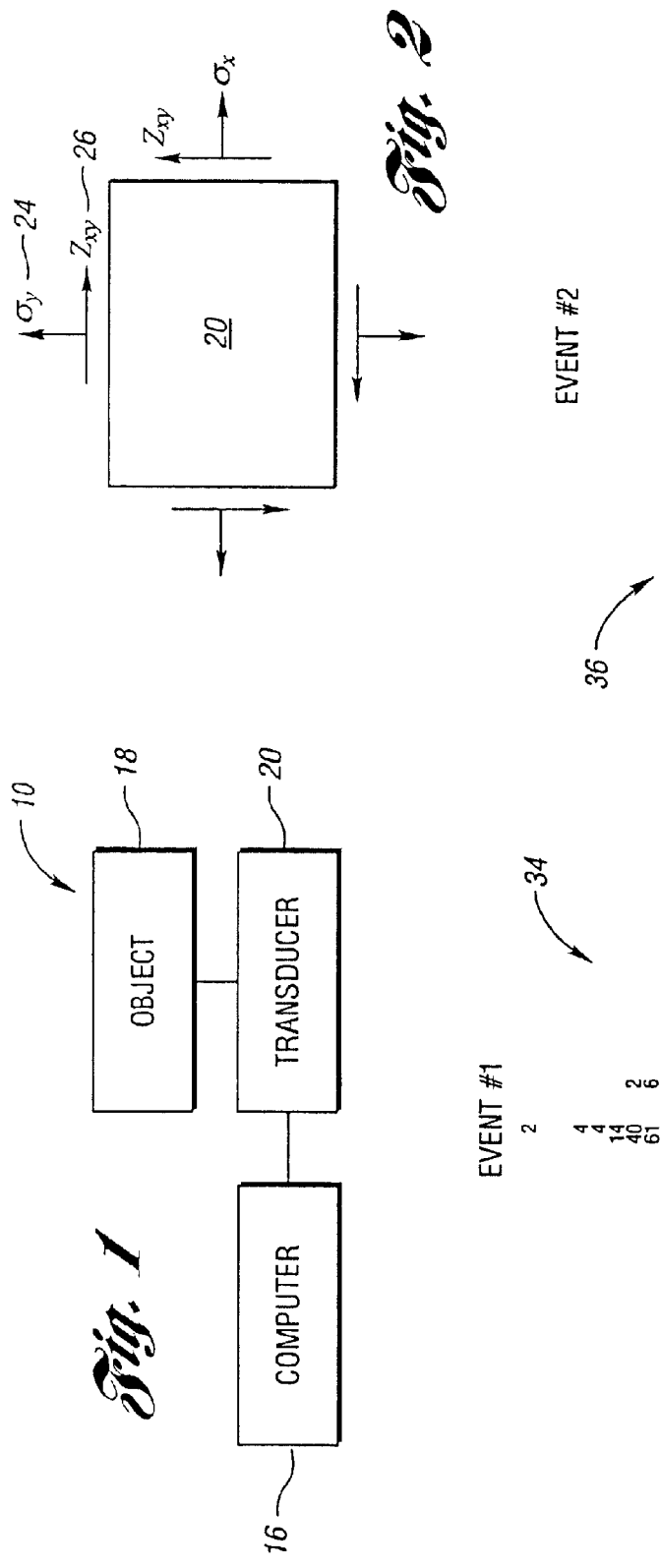
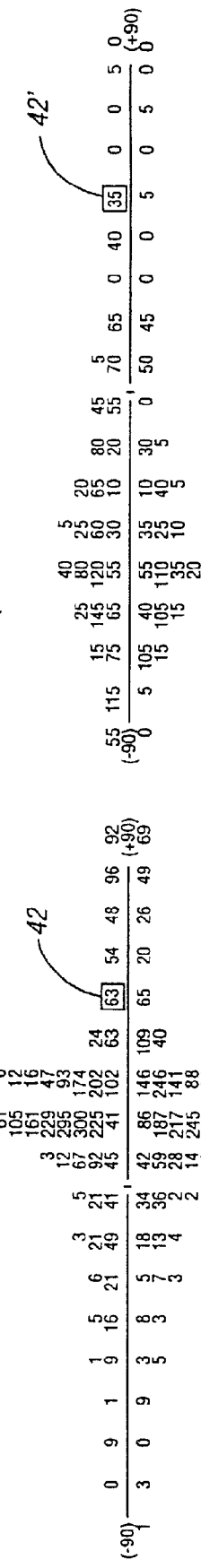

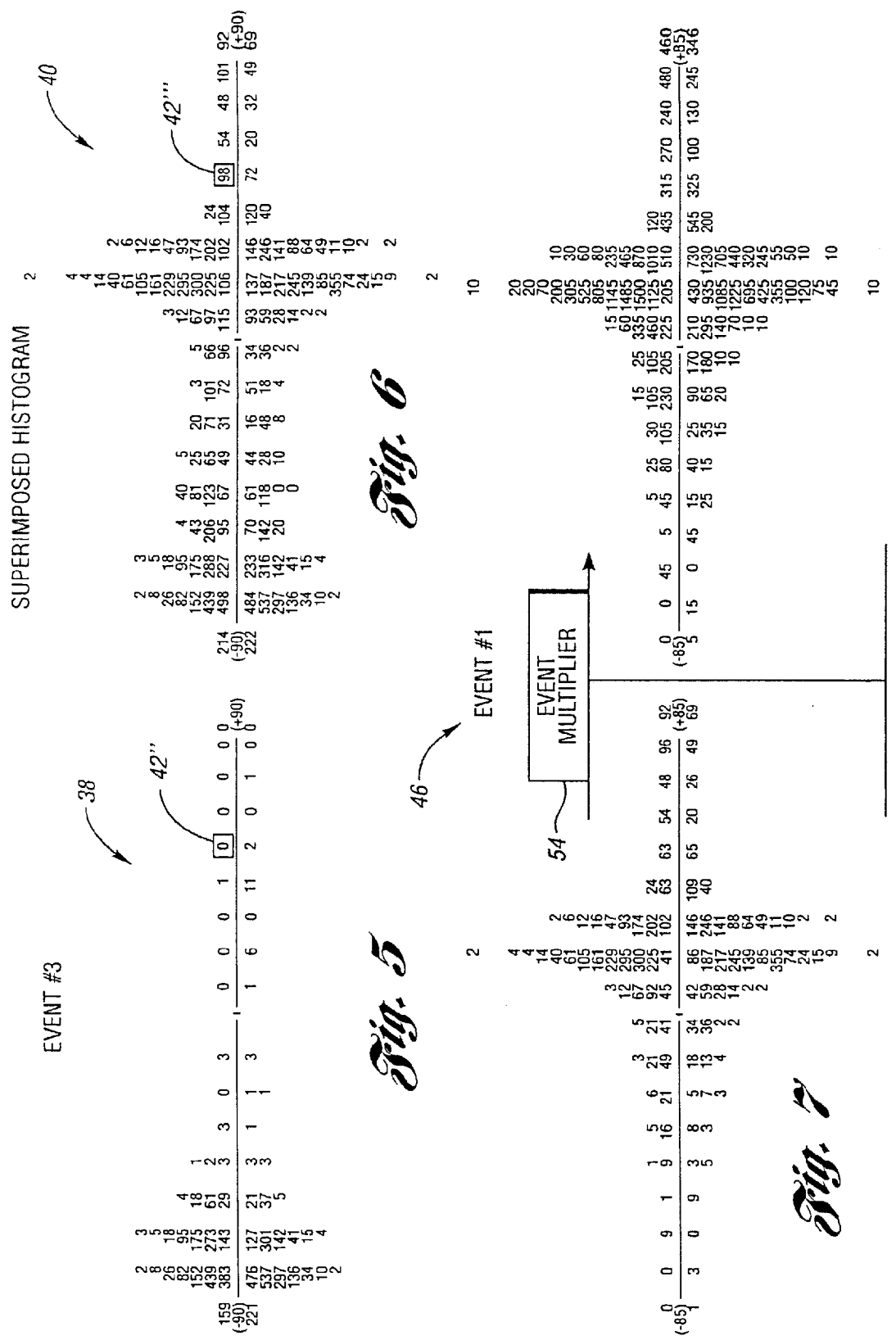

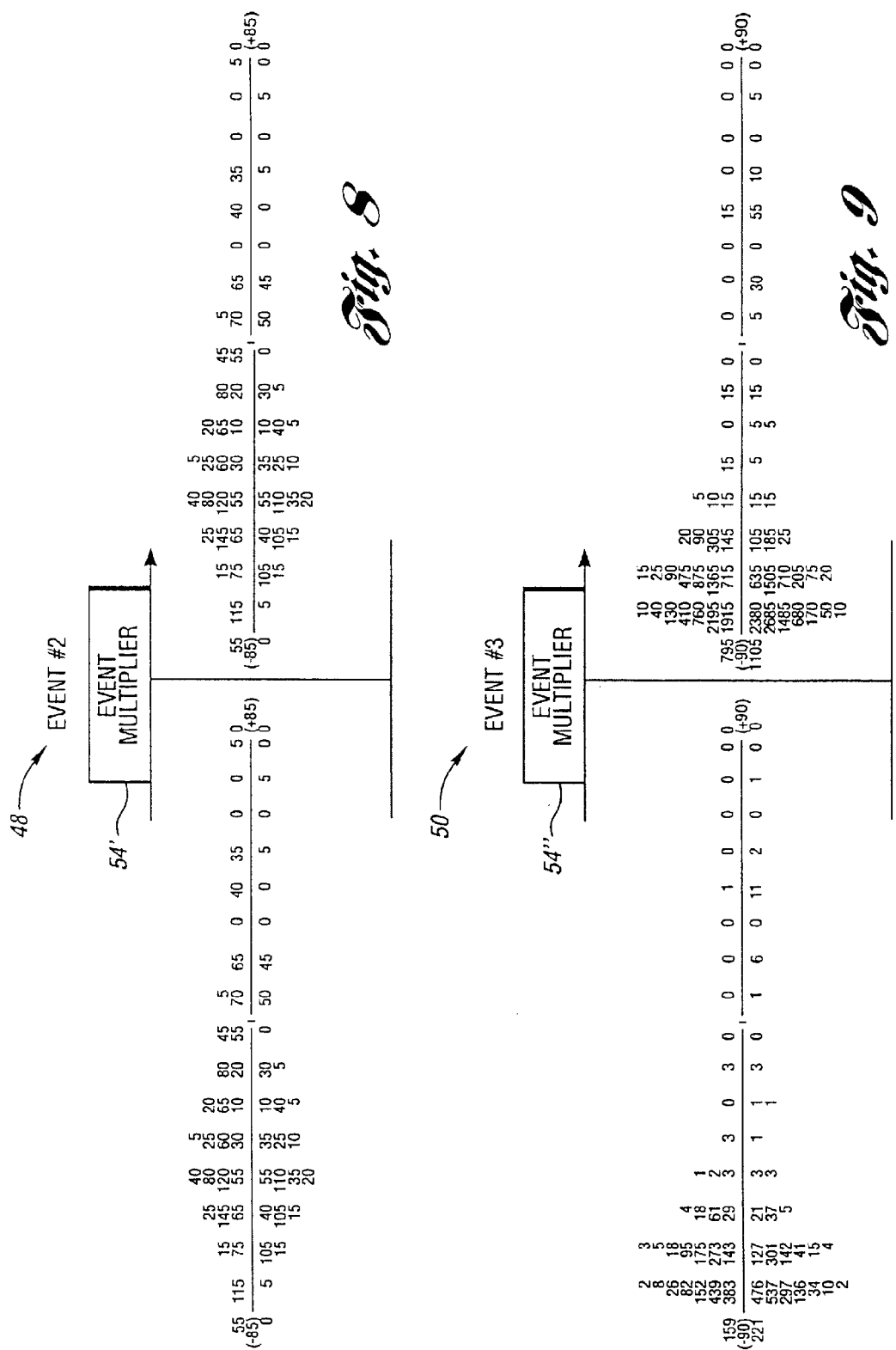

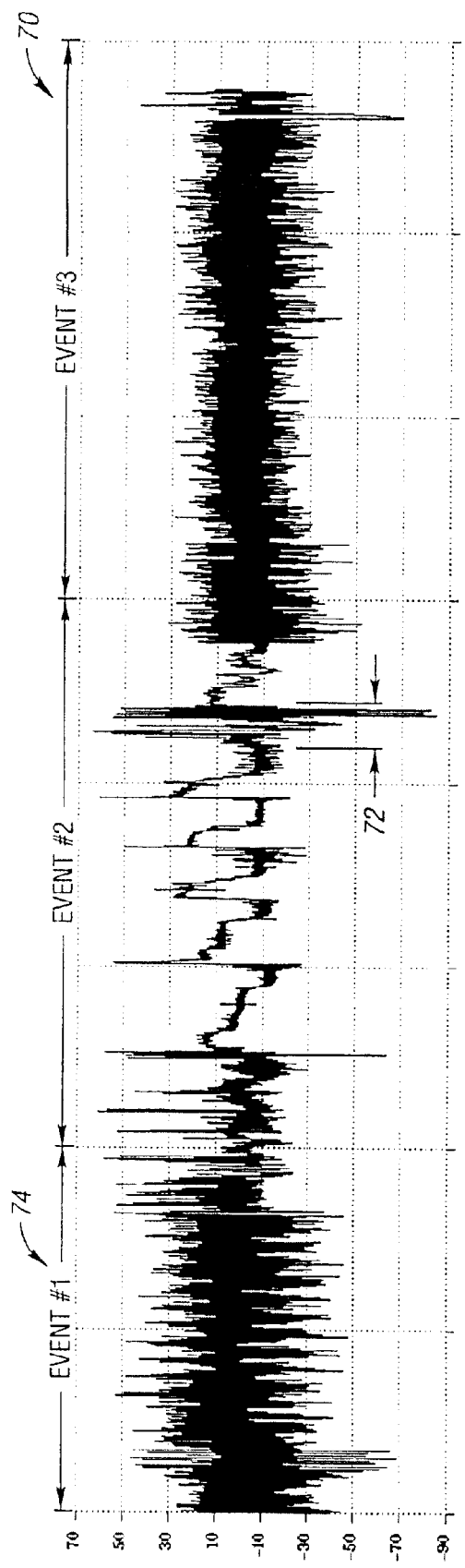
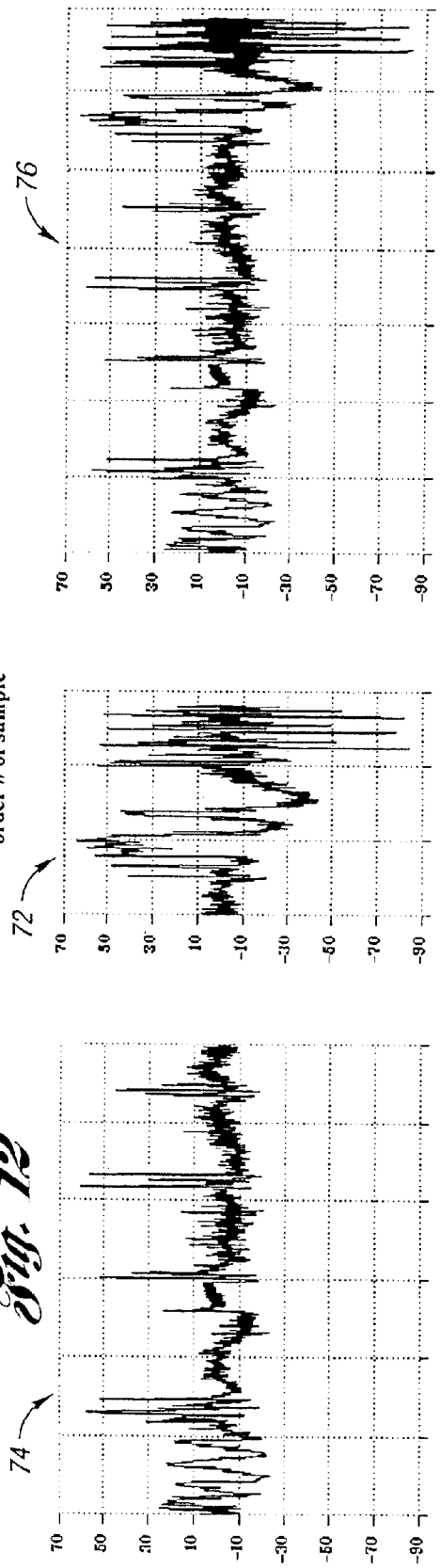
Fig. 12
Fig. 13 sample event #1
Fig. 14 largest stress
Fig. 15 new event #1

US 6,823,740 B1

METHOD OF SELECTING A CRITICAL PLANE FOR MULTI-EVENT FATIGUE LIFE PREDICTION

BACKGROUND OF INVENTION

1. Field of the Invention

The present invention relates to a method of selecting a critical plane for use in predicting fatigue life of an object experiencing multiple stress inducing events.

2. Background Art

Uniaxial fatigue theory is a fatigue life prediction tool. It is used to predict the ability of an object to withstand repeated exposure to stresses before cracking. The process is referred to as "uniaxial" because the prediction is based on one-dimensional stresses being induced within the object.

Critical plane theory is a method to model multi-dimensional stresses as one-dimensional stresses. The one-dimensional stresses can then be analyzed using uniaxial fatigue theory to predict fatigue life. The one-dimensional stresses are determined by selecting a critical plane direction and determining how much stress the multi-dimensional stress exert in the direction of the critical plane.

A problem with the critical plane approach arises when the object experiences a number of stress inducing events. In the past, if there were three events under consideration, three damage calculations would occur relative to three different critical planes. The fatigue life would then be determined by adding together the three damage calculations. This is a problem because the damage calculations are relative to three different critical planes. Accordingly, there exists a need for a method of selecting a critical plane so that the critical plane can be used for the damage calculations of all events. In this manner, damage calculations from each event can be added together for the purposes of calculation fatigue life using uniaxial fatigue theory.

SUMMARY OF INVENTION

The present invention overcomes the foregoing problem with a method for selecting a critical plane. The method analyzes stress induced by multiple events to select a critical plane. The critical plane is suitable for use in calculating damages caused by each event. The present invention thus eliminates the problem of adding together damage calculations made relative to different critical planes.

One aspect of the present invention relates to a method for use with an object experiencing multiple stress inducing events. The method comprises determining a stress distribution histogram for each event and superimposing each stress distribution histogram to create a superimposed stress distribution histogram. A critical plane is determined based on the superimposed stress distribution histogram.

One aspect of the present invention relates to a system for predicting fatigue life of an object experiencing multiple stress inducing events. The system comprises a computer which determines a stress distribution histogram for each event. The stress distribution histograms are superimposed to create a superimposed stress distribution histogram so that the computer can select a critical plane from the superimposed stress distribution histogram.

One aspect of the present invention relates to a method for predicting a fatigue life of an object experiencing multiple stress inducing events. The method comprises determining a stress distribution histogram for each event and weighting at least one of the stress distribution histograms. The method further comprises superimposing each stress distribution histogram to create a superimposed stress distribution histogram. A critical plane is calculated based on the superimposed stress distribution histogram. Once that critical plane is calculated, the stresses induced by each event are adjusted relative to the critical plane. The largest of the adjusted stresses is determined. New events are determined by shifting each event according to the largest stress. This provides mean stress correction. The damage caused by each new event is calculated. The damage associated with the largest stress is subtracted from each of the damage calculations to determine a corrected damage for each of the new events. The corrected damages are added together to determine a total damage. The total damage is used to predict the fatigue life of the object.

BRIEF DESCRIPTION OF DRAWINGS

FIG. 1 illustrates a system in accordance with the present invention;

FIG. 2 illustrates a two-dimensional stress sensor;

FIG. 3 illustrates a stress distribution histogram for an event #1;

FIG. 4 illustrates a stress distribution histogram for an event #2;

FIG. 5 illustrates a stress distribution histogram for an event #3;

FIG. 6 illustrates a superimposed stress distribution histogram;

FIG. 7 illustrates a weighted stress distribution histogram for the event #1;

FIG. 8 illustrates a weighted stress distribution histogram for the event #2;

FIG. 9 illustrates a weighted stress distribution histogram for the event #3;

FIG. 12 illustrates a stress history for multiple stress inducing events;

FIG. 13 illustrates stress history of one event;

FIG. 14 illustrates a portion of the stress history shown in FIG. 15 corresponding with a largest stress; and FIG. 15 illustrates a new event determined in accordance with mean-stress correction.

DETAILED DESCRIPTION

Figure 10:
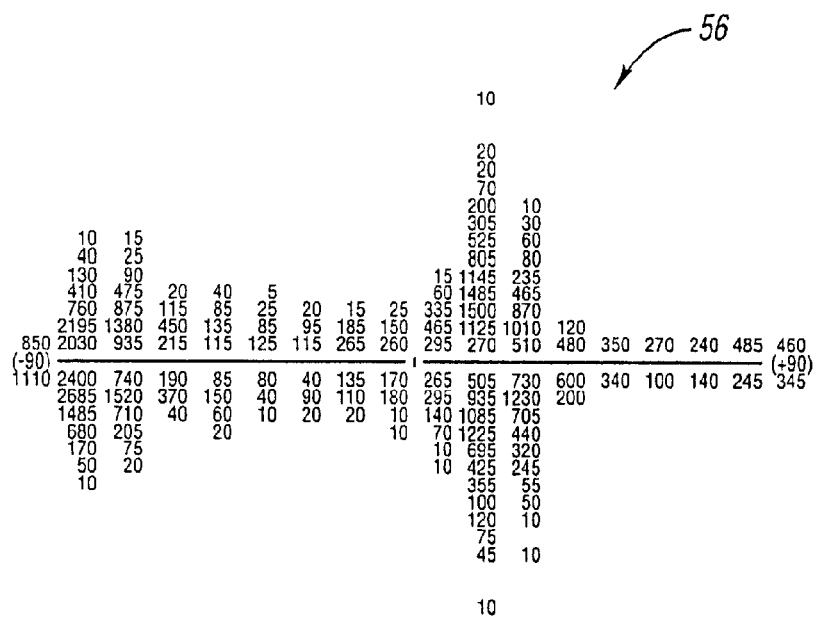
FIG. 10 illustrates a superimposed stress distribution histogram for the weighted stress distributions histograms.

FIG. 1 illustrates a system 10 in accordance with one of the many aspects of the present invention. The system generally comprises a computer 16, an object 18, and a transducer 20. The object 18 experiences multiple stress inducing events. The computer 16 operates in conjunction with the description continued below to predict the fatigue life of the object 18. The prediction is based on a critical plane approach. The critical plane approach of the present invention selects a single critical plane for use in calculating damages caused by each event. Accordingly, the damages caused by each event are calculated with respect to the same critical plane and can be added together to predict fatigue life.

While not intended to limit the present invention, the examples described herein relate to an automotive testing environment. The automotive testing environment subjects automotive vehicles to multiple stress inducing events. Each event induces different multi-dimensional stresses. The present invention can predict the fatigue life of the object with a minimal amount of data regarding the multi-dimensional stresses induced by each event. The prediction can be used for any number of computations, including to design a vehicle component according to desirable performance criteria.

Automotive testing generally comprises driving a vehicle over a number of simulated road conditions. The road conditions simulate driving conditions the vehicle may experience in the future. The performance of the object 18 under the test conditions can provide valuable feedback as to how well the object 18 has been designed to withstand future operation.

Each different road test induces stresses differently within the object 18. Accordingly, each road condition is considered as a separate multi-dimensional stress inducing event. The transducer 20 measures deformation induced by the stresses in the object 18. The computer 16 computates the multi-dimensional stresses induced by the stress inducing event from the deformation. The effect of the stresses on fatigue life is calculated from one run through each event rather than cycling through each event until a crack develops. This approach saves time, computational costs, and allows components to be modeled with less testing time such that further re-designs can be completed with less design revisions.

FIG. 2 illustrates the stresses calculated by the computer 16. As shown, normal 24 and shear 26 stresses are calculated. The calculated stresses are two-dimensional. Only these stresses are calculated because the present invention makes a number of assumption that reduce typical complexity of such calculations. Namely, the typically used nine component stress tensor is reduced to the normal stress 24 and shear stress 26. The reduction is done by assuming (i) the object 18 is relatively thin in comparison to its longitudinal and latitudinal dimensions, (ii) that the stresses occurring throughout the thickness are ignorable as they are relatively insignificant compared to the other stresses, and (iii) that the stresses occurring on opposite sides are equal. However, other assumptions can be made to include more or less stress calculations.

FIGS. 3-5 illustrate histograms for three events referred to as event #1, event #2, and event #3, which are respectively referred to with reference numerals 34, 36, and 38. The histograms are a means to track the stresses induced by each event. The histograms are generated by the computer. The computer breaks up each event into a number of time intervals. The stresses (normal stress 24 and shear stress 26) induced by each event are calculated for the time period. A principle stress and an angle of the principle is used to represent the stresses as a one-dimensional stress. The principle stress represents in one-dimension the cumulative effect of the normal stress 24 and the shear stress 26. The angle represents a direction of the principle stress.

The histograms utilize a binning system to track occurrences of the principle stresses and angles over the period of time that the object experiences stresses. The principle stress must have an average value within a bin for a predetermined period of time to count as an occurrence. The binning system organizes the principle stresses along a vertical axis and the angles along a horizontal axis. The vertical axis includes a range from 0 to 100 MPa and 0 to −100 MPA. The ranges span positive and negative bins of 0–10, 10–20, 20–30, 40–50, 50–60, 60–70, 70–80, 80–90, and 90–100 MPA. The horizontal axis includes a range from 0–90° and 0 to −90°. The ranges span positive and negative bins of 0–10, 10–20, 20–30, 30–40, 50–60, 60–70, 70–80, and 80–90. Please note, the angles and principle stresses are relative to the center of the stress plane shown in FIG. 2.

FIG. 6 illustrates the superimposing of the histograms shown in FIGS. 3-5 to create a superimposed histogram 40. The single critical plane is selected from the superimposed histogram. This overcomes the problem of adding together damages calculated relative to different critical planes by determining a single critical plane for all the events. The damages caused by each event can then be determined with respect to the same critical plane. Damages calculated with respect to the same critical plane can be added together to predict fatigue life.

The superimposed histogram 40 is formed by adding together the occurrence from each event that fall within common bins. For example, in exemplary bin 42, event #1 includes 63 occurrences of a principle stress with an amplitude in the range of 0–10 MPA and an angle in the range of 40–50 degrees, bin 42' of event #2 similarly includes 35 occurrences, and event bin 42" of #3 similarly includes 0 occurrences for a superimposed bin 42''' total of 98 occurrences. The same process is repeated for each bin to populate each bin in the superimposed histogram 40. The single critical plane is then selected from the superimposed histogram 40 by a computer or other device. This allows the effects from each event to be included when selecting a single critical plane.

FIGS. 7-10 illustrate an aspect of the present invention in which the histograms are weighted prior to superimposing the histogram. The weighting is done so that some events can affect fatigue life more than the other events. The weighted histograms of events #1 to #3 are respectively referred to with reference numerals 46, 48, and 50. For exemplary purpose, it is assumed that event #1 and event #3 are run five times for each time event #2 is run. Rather than run each event #1 and #3 over and over again, the present invention multiples a single run of the event with an event multiplier 54.

As shown in FIG. 7, the event multiplier 54 of event #1 is five as event #1 is to be run five times. As shown in FIG. 8, the event multiplier 54' of event #2 is one as event #2 is to be run only once. As shown in FIG. 9, the event multiplier 54" of event #3 is five as event #3 is to be run five times. The event multiplier 54 can be the same or different for each event. The event multiplier 54 weights the importance of each event to correspond with the need to simulate some events more than others.

FIG. 10 illustrates weighted superimposed histogram 56. The weighted superimposed histogram 56 is determined by adding the occurrences of each principle stress magnitude after application of the event multiplier 54. The critical plane is then calculated based on the weighted superimposed histogram 56.

Figure 11:
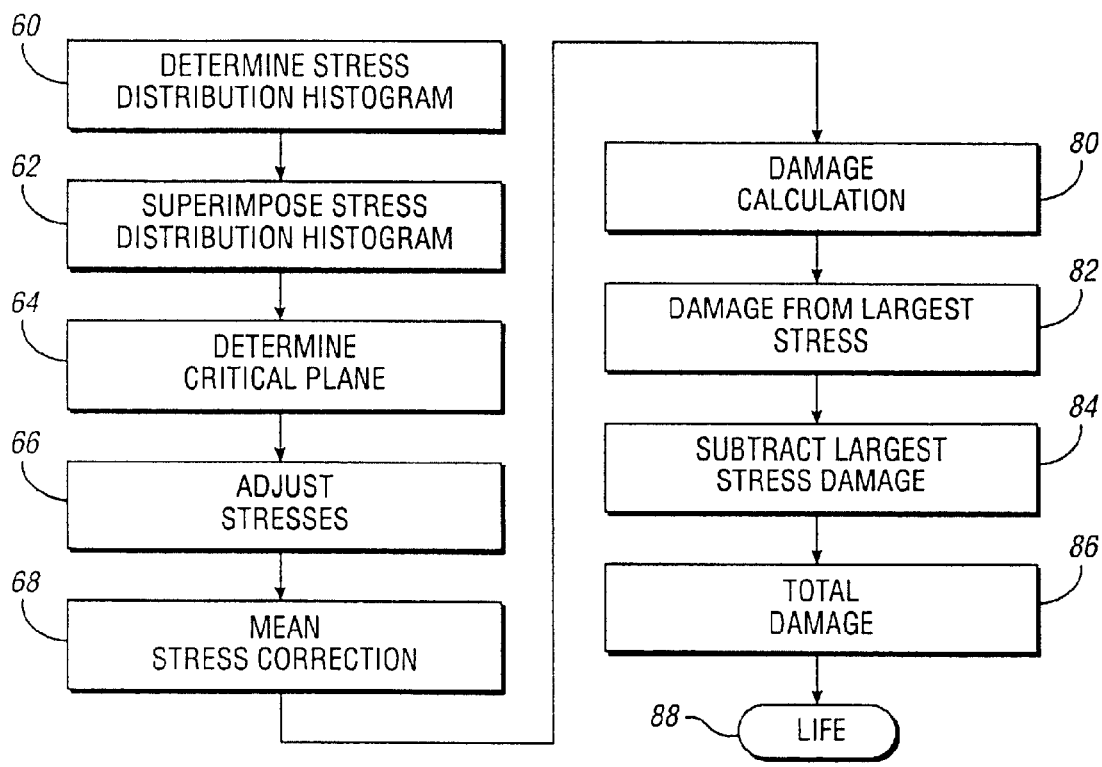
FIG. 11 illustrates a method for predicting a fatigue life of the an object experiencing multiple stress inducing events.

FIG. 11 illustrates a method for predicting a fatigue life of an object experiencing multiple stress events in accordance with one aspect of the present invention. The method comprises a step 60 to determine a stress distribution histogram for each event. A step 62 superimposes each stress distribution histogram to create a superimposed stress distribution histogram. A step 64 calculates a critical plane based on the superimposed stress distribution histogram.

A step 66 adjusts the principle stresses shown in the histograms for each event relative to the direction of the critical plane calculated in step 64. Once the principle stresses for each event are computed relative to the same critical plane, the damages caused by each event can be calculated and added together to determine the fatigue life of the object.

Prior to calculating the damages, and in accordance with another aspect of the present invention, the precision of the life expectancy calculation is improved at a step 68 with mean stress correction. The mean stress correction is typically done in accordance with the Smith-Watson-Topper rule, as understood by one of ordinary skill in the art. Mean stress correction is shown with more detail in FIGS. 12-15.

FIG. 12 illustrates a history graph 70. The history graph 70 illustrates all the principle stresses for each of the events after adjustment to the critical plane direction. The vertical axis is MPa and the horizontal axis is a cycle reference number. In the real world the vehicle is already prestressed, therefore, the prestressing produces a non-zero mean stress environment. As such, each induced stress has a non-zero mean stress. This can be a problem. The problem occurs because fatigue life calculations determined under non-zero mean stress tend to be incompatible with fatigue life calculations based on zero mean stress. This problem is ameliorated with mean stress correction.

Mean stress correction comprises identifying each event within the history and shifting each event according to a largest stress portion 72 found the history. Once shifted, the events become new events. Damages are then calculated based on the new events.

The mean stress correction is understood by one skilled in the art and can be generally understood with respect to event #1. FIG. 13 illustrates a portion 74 of history graph 70 that corresponds with event #1. FIG. 14 illustrates the largest stress portion 72. Mean stress correction of event #1 is shown in FIG. 15 and occurs when the event #1 portion 74 is shifted according to the largest stress portion 72. A new event #1, which is referred to with reference numeral 76, is created. The same shifting occurs for each event. The damages are then calculated from the new events such that mean stress correction can be incorporated and used to improve the precision of the damage calculations.

Returning to FIG. 13, a step 80 calculates damages caused by each new event according to the Palmgren-Miner Rule. Because the stresses were adjusted relative to the same critical principle plane, the damage calculations are in the same critical plane direction. Accordingly, the damage caused by each event can be added without the problems experienced by adding damages having different critical planes.

The damages caused by each new event are inflated from adding the largest stress to each new event. Accordingly, the portion of the damages attributable to the largest stress portion 72 must be eliminated. The method includes a step 82 for calculating the damage caused by the largest stress portion 72. A step 84 is also included for subtracting the damage calculated for the largest stress from the damages calculated for each of the new events to determine corrected damage for each of the new events.

The method includes a step 80 for calculating the total damage from each new event based on the corrected damages. The total damages are calculated by adding together each of the corrected damage calculations. This can be done since the damages are calculated in the same critical plane direction and with the same mean stress correction. From the total damage, a step 88 calculates the fatigue life. The life is calculated according to Palmgren-Miner Rules by taking the inverse of the total damages.

The computer 16 can be used to implement the method according to FIG. 13. More specifically, the computer can include a computer-implemented software program for predicting a life expectancy of an objected subjected to multiple stress inducing events as described above. The software program can be stored on a disc or other medium and loaded to a computer or other device for use in predicting life expectancy.

While the best mode for carrying out the invention has been described in detail, those familiar with the art to which this invention relates will recognize various alternative designs and embodiments for practicing the invention as defined by the following claims.

What is claimed is:

1. A method for use with an object experiencing multiple stress inducing events, the method comprising:
    determining a stress distribution histogram for each event;
    superimposing each stress distribution histogram to create a superimposed stress distribution histogram; and calculating a critical plane based on the superimposed stress distribution histogram.

2. The method of claim 1 further comprising predicting the fatigue life of the object experiencing the multiple stress inducing events, wherein the prediction is based on the critical plane calculated from the superimposed stress distribution histogram.

3. The method of claim 2 wherein superimposing the stress distribution histograms comprises adding together at least two stress distribution histograms.

4. The method of claim 3 wherein predicting fatigue life comprises calculating a total damage caused by each event relative to the critical plane.

5. The method of claim 3 wherein calculating total damage further comprises (i) determining a mean stress correction factor; (ii) calculating the damage caused by each event in accordance with the mean stress correction factor; (iii) subtracting a damage error attributable to the mean stress correction factor from the damages calculated for each event; and (iv) adding together the damages calculated for each event after subtracting the damage attributable to the mean stress correction factor, wherein the damages are accurately added together because the damages are calculated with respect to the same critical plane.

6. The method of claim 5 wherein the mean stress correction factor is a largest stress determined from stress for all the events.

7. The method of claim 1 wherein superimposing the stress distribution histograms comprises weighting at least one of the stress distribution histograms prior to superimposing each stress distribution histogram.

8. The method of claim 7 wherein weighting comprises multiplying at least one of the stress distribution histograms by a correction factor.

9. The method of claim 1 further comprising adjusting the stress induced by each event relative to the critical plane and calculating damage caused by each event based on the adjusted stresses for use in predicting fatigue life.

10. The method of claim 1 wherein each stress distribution histogram includes a number of histogram bins populated with occurrences of principle stresses, and wherein superimposing the stress distribution histograms comprises adding together occurrences in common bins from all the events.

11. The system of claim 2 wherein superimposing the stress distribution histograms comprises adding together at least two stress distribution histograms.

12. The system of claim 3 wherein predicting the fatigue life is based on a total damage to the object and the total damage is calculated by (i) determining a mean stress correction factor; (ii) calculating the damage caused by each event in accordance with the mean stress correction factor; (iii) subtracting a damage error attributable to the mean stress correction factor from the damages calculated for each event; and (iv) adding together the damages calculated for each event after subtracting the damage attributable to the mean stress correction factor, wherein the damages are accurately added together because the damages are calculated with respect to the same critical plane.

13. The system of claim 12 wherein the mean stress correction factor is a largest stress determined from stress for all the events.

14. system for predicting fatigue life of an object experiencing multiple stress inducing events, the system comprising:
   a computer for receiving signals from a deformation sensor, wherein the deformation sensor measures deformation of the object experiencing the multiple stress inducing events;
   the computer calculating stresses for each event from the measured deformation, determining a stress distribution histogram for each event, superimposing each stress distribution histogram to create a superimposed stress distribution histogram, and calculating a critical plane based on the superimposed stress distribution histogram.

15. The system of claim 14 further comprising predicting a fatigue life of the object experiencing the multiple stress inducing events, wherein the prediction is based on the critical plane calculated from the superimposed stress distribution histogram.

16. The system of claim 14 wherein superimposing the stress distribution histograms comprises weighting at least one of the stress distribution histograms prior to superimposing each stress distribution histogram.

17. The system of claim 16 wherein weighting comprises multiplying at least one of the stress distribution histograms by a correction factor.

18. The method of claim 14 further comprising adjusting the stress induced by each event relative to the critical plane and calculating damage caused by each event based on the adjusted stresses for use in predicting fatigue life.

19. The method of claim 14 wherein each stress distribution histogram includes a number of histogram bins populated with occurrences of principle stresses, and wherein superimposing the stress distribution histograms comprises adding together occurrences in common bins from all the events.

20. A method for predicting a fatigue life of an object experiencing multiple stress inducing events, the method comprising:
   determining a stress distribution histogram for each event;
   weighting at least one of the stress distribution histograms;
   superimposing each stress distribution histogram to create a superimposed stress distribution histogram;
   calculating a critical plane based on the superimposed stress distribution histogram;
   adjusting the stresses induced by each event relative to the critical plane;
   determining a largest of the adjusted stresses stress;
   determining new events by shifting each event based on the largest stress;
   calculating damage caused by each new event;
   calculating damage caused by the largest stress;
   subtracting the damage caused by the largest stress from the damage calculated for each new event to determine corrected damage for each new event;
   calculating total damage by adding together the corrected damages calculated for each new event; and predicting the fatigue life of the object based on the total damage.

* * * * *